United States Patent [19]

Oliff et al.

[11] Patent Number: 5,028,692

[45] Date of Patent: Jul. 2, 1991

[54] GASTRIN RELEASING PEPTIDE ANTAGONIST

[75] Inventors: Allen I. Oliff, Gwynedd Valley; Walfred S. Saari, Lansdale, both of Pa.

[73] Assignee: Merck & Co., Inc., Rahway, N.J.

[21] Appl. No.: 343,092

[22] Filed: Apr. 25, 1989

[51] Int. Cl.$^5$ .......................... C07K 7/30; C07K 7/06; C07K 7/02; A61K 37/43

[52] U.S. Cl. .................... 530/329; 530/309; 530/332; 530/345

[58] Field of Search ............... 530/332, 329, 309, 345; 514/16, 17

[56] References Cited

U.S. PATENT DOCUMENTS 4,435,385  3/1984  Bauer et al. ........................ 424/177

OTHER PUBLICATIONS

Jensen et al., (1984) Nature, 309:61–63.
Marki et al., (1981) J. Am. Chem. Soc., 103:3178–3185.
Tenbrink, (1987) J. Org. Chem., 52:418–422.

*Primary Examiner*—Jeffrey E. Russel
*Assistant Examiner*—Kay Kim
*Attorney, Agent, or Firm*—Frank P. Grassler; Donald J. Perrella; Hesna J. Pfeiffer

[57] ABSTRACT

Small cell lung carcinoma cells (SCLC) contain gastrin releasing peptide (GRP) receptors. The response of the cells to GRP is rapid growth. We have found a group of peptide derivatives that act as GRP antagonists by blocking the binding of GRP to its receptor thereby inhibiting the growth of cells that are sensitive to the growth promoting activity of GRP.

2 Claims, No Drawings

GASTRIN RELEASING PEPTIDE ANTAGONIST

BACKGROUND OF THE INVENTION

Gastrin releasing peptide (GRP), a 27-amino acid hormone, stimulates the growth of small cell lung carcinoma (SCLC) cells in cell culture. Antibodies directed against GRP block the growth of SCLC in nude mice.

DISCLOSURE STATEMENT

Broccardo et al., Br. J. Pharmac. 55:221–227 (1975) compare the pharmacological activity of two natural bombesin like peptides and 25 related synthetic peptides to that of bombesin.

Marki et al., Peptides 2, Suppl. 2:169–177 (1981) disclose structure activity relationship of 26 peptide analogs of bombesin and GRP. The minimal essential residues required for full potency of bombesin-like effects is represented by an acetylated C-terminal 8 peptide fragment wherein position 7 can be substituted by alanine, histidine, glutamine or D-glutamine. Modification of the tryptophan [8] and histidine [12] residues by alanine abolished the biological potency of these peptides. A blocked N terminus is necessary for maximum response.

Moody et al., Peptides 4 (5):683–686 (1983) disclose the presence of high concentrations of bombesin-like peptides and receptors in small cell lung cancer (SCLC) and suggest that bombesin may function as an important regulatory agent in human SCLC.

Jensen et al., Nature 309:61–63 (3 May 1984) disclose that a substance P analog is also a bombesin receptor antagonist.

Weber et al., J. Clin. Invest. 75:306–309 (1985) disclose that the mitogenicity of gastrin releasing peptide (GRP) resides in its carboxy terminal fragment, designated GRP 14–27, which is partly homologous to bombesin. The authors speculate that GRP or a closely related small peptide may be acting as an autocrine growth factor for SCLC.

Cuttitta et al., Nature, 316:823–826 (29 Aug. 1985) disclose that a monoclonal antibody to bombesin blocks the binding of the hormone to cellular receptors and inhibits the clonal growth of SCLC in vitro and the growth of SCLC xenografts in vivo demonstrating that bombesin like peptides can function as autocrine growth factors for human SCLC.

Corps et al., Biochem. J. 231:781–784 (1985) disclose that an analog of substance P inhibits the stimulation of DNA synthesis induced in Swiss 3T3 cells by bombesin.

Bepler et al., Cancer Research 47:2371–2375 (1 May 1987) disclose that the undecapeptide physalaemin inhibits the clonal and mass culture growth of SCLC cell lines at picomolar concentrations.

Heinz-Erian et al., Am. J. Physiol. 252:G439–G442(1987) disclose that [D-Phe$^{12}$] analogs of bombesin are the only bombesin receptor antagonists identified to date that interact only with the bombesin receptor.

Coy et al., J. Biol. Chem. 263(11):5056–5060 (1988), disclose that [Leu$^{14}$-ψ-CH$_2$NH-Leu$^{13}$] bombesin exhibits a 100-fold improvement in binding affinity compared to previously reported bombesin receptor antagonists and is also a potent inhibitor of bombesin-stimulated growth.

Woll et al., Biochem. Biophys Res. Comm. 155(1): 359–365 (1988), disclose that [Leu$^{13}$-ψ-(CH$_2$NH)Leu$^{14}$]bombesin is a specific bombesin receptor antagonist in Swiss 3T3 cells.

OBJECTS OF THE INVENTION

It is an object of the present invention to provide peptide derivatives that act as antagonists of GRP. Another object is to provide methods for preparing these peptide derivatives. These and other objects of the present invention will be apparent from the following description.

SUMMARY OF THE INVENTION

A series of peptide derivatives have been found which are GRP antagonists and which suppress GRP-stimulated mitogenesis in Swiss 3T3 cells.

The peptide derivatives of the present invention have the following formula:

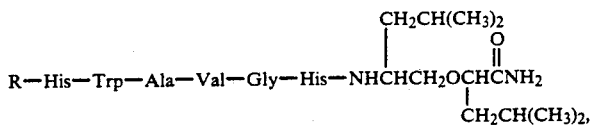

R is

or R'SO$_2$ wherein R' is an alkyl radical of 1 to 6 carbon atoms, the amino acids possess the natural L-configuration, and any one optically active amino acid may be substituted by its D isomer or glycine.

DETAILED DESCRIPTION OF THE INVENTION

The activity of the peptide derivatives of the present invention as GRP antagonists was determined in competitive binding assays with a radioactive GRP derivative. Swiss 3T3 fibroblasts were used in these tests as the source of GRP receptor. Because these cells respond to GRP binding with a rapid increase in DNA synthesis, compounds that bind to the GRP receptor can also be tested for their ability to stimulate DNA synthesis. New DNA synthesis is one of the early steps in cell division and is widely accepted as a measure of mitogenicity or cell growth. Compounds which bind to the receptor and do not stimulate growth are then tested for their ability to block GRP stimulated DNA synthesis. Compounds which block DNA synthesis are mitogenic antagonists. The efficacy of these antagonists against the GRP receptor on SCLC was demonstrated by measuring inhibition of GRP-dependent calcium release in these cells.

The peptidyl moiety of the peptide derivatives present invention can be synthesized from their constituent amino acids by conventional peptide synthesis techniques, preferably by solid-phase technology. The peptides are then purified by reverse-phase high performance liquid chromatography (HPLC).

Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al , "The Peptides: Analysis, Synthesis, Biology" 2, Chapter 1, Academic Press, 1980. The teachings of these works are hereby incorporated by reference.

The compounds of the present invention have the formula

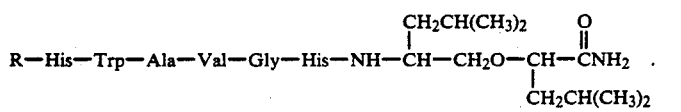

These compounds are obtained by reacting a compound of the formula

with an amide protected compound of the formula

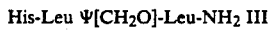

This reaction may be carried out under peptide fragment condensation conditions, for example, by reacting the compound of formula II with the compound of formula III in the presence of a catalyst such as 1-hydroxybenzotriazole, a base such as triethylamine and a condensing agent such as dicyclo hexylcarbodimide, in a polar solvent such as dimethyl formamide (DMF) at about room temperature under an inert atmosphere such as $N_2$ for an extended time such as about 10 to 30 hours.

The compound of formula II is prepared under any convenient method for effecting peptide synthesis. The compound of formula III is prepared starting from the known compound (S,S)-BOC-Leu Ψ[CH₂O]-Leu-OH. This compound is converted to its corresponding amide of the formula

and then is deprotected to give the compound

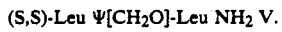

Compound V is reacted with Nα-Nim-bis-BOC-(S)-histidine ethyl acetate solvate to give the compound

Compound VI is deprotected and converted to its dihydrochloride of the formula

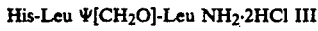

and reacted with a compound of formula II to give the final compound of formula I.

The following examples illustrate the present invention without, however, limiting the same thereto.

EXAMPLE 1

Step 1. (S,S)-BOC-Leu Ψ[CH₂O]-Leu-NH₂

A mixture of (S,S)-BOC-Leu Ψ[CH₂O] Leu-OH (3.03 g, 9 14 mmol), prepared by the method of R. E. Ten Brink, J. Org. Chem., 52, 418 (1987), 4-methyl morpholine (1.0 mL, 9.14 mmol) and isobutyl chloro formate (1.2 mL, 9.14 mmol) in ethyl acetate (100 mL) was stirred in an ice bath under $N_2$ for 15 minutes. Concentrated ammonium hydroxide (1.3 mL, 20 mmol) was added. After stirring in the ice bath for 10 minutes, the reaction mixture was then stirred at room temperature for 18 hours. The reaction was washed sequentially with 10% citric acid, brine, saturated $NaHCO_3$ solution and brine and the ethyl acetate solution then dried ($Na_2SO_4$), filtered and concentrated under reduced pressure. Flash chromatography over silica gel and elution with a mixture of 5% methanol-95% methylene chloride gave 4.0 g of solid amide. An analytical sample, mp 162°-65°, was obtained upon recrystallization from ethyl acetate hexane.

Calcd. for $C_{17}H_{34}N_2O_4$: C, 61.78; H, 10.37; N, 8.48. Found: C, 61.86; H, 10.71; N, 8.45.

Step 2. (S,S)-Leu Ψ[CH₂O]-Leu-NH₂

A slurry of the BOC derivative from Step 1 (4.0 g) and ethyl acetate (200 mL) was stirred and cooled in an ice bath and saturated with HCl gas for 10 minutes. After stirring in the ice bath for 1 hour, solvent was removed under reduced pressure and the residue dried to give the deprotected amide.

Step 3. (BOC)₂-His-Leu Ψ[CH₂O]-Leu-NH₂

A mixture of Nα-Nim bis-BOC-(S)-histidine ethyl acetate solvate (1.44 g, 3.75 mmol), 4-methylmorpholine (0.42 mL, 3.75 mmol) and isobutylchloroformate (0.49 mL, 3.75 mmol) in ethyl acetate (50 mL) was stirred in an ice bath under $N_2$ for 20 minutes. The HCl salt (1.0 g, 3.75 mmol) from Step 2 was added followed by 4-methylmorpholine (0.42 mL, 3.75 mmol) and the reaction mixture stirred in the ice bath for 30 minutes and then at room temperature for 18 hours. After washing with 10% citric acid, brine, saturated $NaHCO_3$ solution and brine, the ethyl acetate extract was dried ($Na_2SO_4$), filtered and concentrated under reduced pressure. Flash chromatography over silica gel and elution with 3% methanol-97% methylene chloride gave 1.4 g of product. An analytical sample, mp 126°-33° dec., was obtained upon recrystallization from ethyl acetate hexane.

Calcd. for $C_{28}H_{49}N_5O_7$; C, 59.23; H, 8.70; N, 12.34. Found: C, 58.87; H, 9.01; N, 12.30.

Step 4. His-Leu Ψ[CH₂O]-Leu-NH₂·2HCl

A solution of the bis BOC derivative from Step 3 (1.3 g) in ethyl acetate (150 mL) was cooled in an ice bath

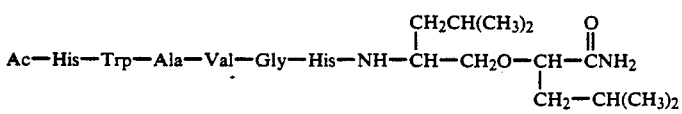

and saturated with HCL gas for 10 minutes. After stirring at ice bath temperature for 45 minutes, solvent was removed under reduced pressure and the residue recrystallized from methanol-ethyl acetate to give the deprotected dihydrochloride salt.

Calcd. for $C_{18}H_{33}N_5O_3 \cdot 2HCl$: C, 49.08; H, 8.01; N, 15.90; Cl, 15.90. Found: C, 48.53, H, 8.05; N, 15.60; Cl, 15.91.

Step 5. 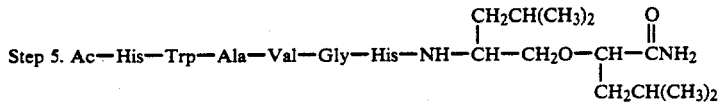

A solution of His-Leu $\Psi[CH_2O]$-Leu $NH_2 \cdot 2HCL$ (40.4 mg, 100 μmol), Ac His-Trp-Ala Val Gly-OH (46 mg, 59 mmol), 1 hydroxybenzotriazole (10.8 mg), dicyclohexylcarbodiimide (14.4 mg, 70 μmol) and triethylamine (28 μL, 200 μmol) in DMF (2 mL) was stirred at room temperature under $N_2$ for 20 hours. After concentrating under reduced pressure, the residue was partitioned between 5 mL each of water and ethyl acetate and filtered. The aqueous extract was washed with fresh ethyl acetate, filtered and lyophilized to give a white powder. This product was purified by preparative HPLC to give the title peptide.

EXAMPLE 2

$CH_3SO_2NH$-His-Trp-Ala-Val-Gly-His-Leu $\Psi[CH_2O]$-Leu-$NH_2$

Step 1. $CH_3SO_2NH$-His-Trp-Ala-Val-Gly-OH

This peptide is prepared by a standard solid phase procedure beginning with BOC glycyl resin with additional amino acids added with DCC coupling. The mesyl group is added by reaction of the primary amine with methane sulfonyl chloride in DMF in the presence of triethyl amine.

Step 2. $CH_3SO_2NH$-His-Trp-Ala-Val-Gly-His-Leu $\Psi[CH_2O]$-Leu-$NH_2$

This peptide is prepared by coupling the His-Leu $\Psi[CH_2O]$-Leu-$NH_2$ intermediate of Step 4, Example 1 with the peptide from Step 1 of this Example following the method of Step 5, Example 1. Pure product is obtained by preparative HPLC.

EXAMPLE 3

BOC-NH-His-Trp-Ala-Val-Gly-His-Leu $\Psi[CH_2O]$-Leu-$NH_2$

Step 1. BOC-NH-His-Trp-Ala-Val-Gly-OH

This peptide is prepared by a standard solid phase procedure beginning with BOC glycyl resin with additional amino acids added with DCC coupling. The BOC group is added by reaction of the primary amine with di-tert.-butyl dicarbonate under standard reaction conditions.

Step 2. BOC-NH-His-Trp-Ala-Val-Gly-His-Leu $\Psi[CH_2O]$-Leu-$NH_2$

The peptide of Step 1 is coupled with the His-leu $\Psi[CH_2O]$ Leu-$NH_2$ intermediate of Step 4, Example 1 following the method of Step 5, Example 1. Pure product is isolated by preparative HPLC.

What is claimed is:

1. A compound of the formula:

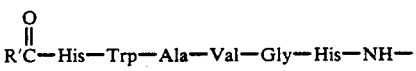
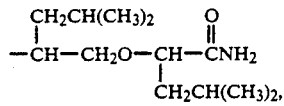

wherein R′ is an alkyl radical of 1 to 6 carbon atoms, the amino acids possess the natural L-configuration and any one optically active amino acid may be substituted by its D-isomer or by glycine.

2. A compound of claim 1 wherein R′ is methyl.

* * * * *